(12) United States Patent
Losack

(10) Patent No.: US 10,524,888 B1
(45) Date of Patent: Jan. 7, 2020

(54) ORAL HYGIENE SYSTEM

(71) Applicant: Vincent Losack, Corrales, NM (US)

(72) Inventor: Vincent Losack, Corrales, NM (US)

( * ) Notice: Subject to any disclaimer, the term of this patent is extended or adjusted under 35 U.S.C. 154(b) by 589 days.

(21) Appl. No.: 15/283,067

(22) Filed: Sep. 30, 2016

(51) Int. Cl.
*A61C 17/02* (2006.01)
*A61C 17/032* (2006.01)
*A61H 13/00* (2006.01)

(52) U.S. Cl.
CPC ........ *A61C 17/0202* (2013.01); *A61C 17/032* (2019.05); *A61H 13/005* (2013.01)

(58) Field of Classification Search
CPC . A61H 1/00; A61H 7/00; A61H 7/002; A61H 7/003; A61H 7/007; A61H 2205/108; A61H 13/00; A61H 13/005; A61H 33/00; A61H 9/00; A61H 9/0021; A61H 9/0028; A61C 17/0202; A61C 17/0214; A61C 17/00; A61C 17/028; B01F 5/0413; B05B 7/0425; B05B 7/2405; B05B 7/2443; B05B 7/30; B05B 7/0408; B05B 7/2478; E03C 1/046; A62C 5/02
USPC ..... 433/80–90; 137/151, 123, 893; 222/133, 222/630, 464.1, 145.5, 567, 570
See application file for complete search history.

(56) References Cited

U.S. PATENT DOCUMENTS

| | | | | |
|---|---|---|---|---|
| 1,868,893 A | * | 7/1932 | Gentle | A61M 3/0233 128/200.21 |
| 2,058,901 A | * | 10/1936 | Mcpherson | B01F 5/0496 422/266 |
| 2,231,782 A | * | 2/1941 | Thompson | B05B 7/12 239/311 |
| 2,302,799 A | * | 11/1942 | Peterson | A01C 23/042 111/7.1 |
| 2,785,838 A | * | 3/1957 | Mayer, Jr. | B65D 83/14 222/402.14 |
| 2,850,323 A | * | 9/1958 | Veres | B23Q 11/1084 239/354 |
| 3,042,314 A | * | 7/1962 | Packard | B05B 7/2443 239/310 |
| 3,164,153 A | * | 1/1965 | Zorzi | A61C 17/00 433/216 |
| 3,225,759 A | * | 12/1965 | Drapen | A61C 1/0084 137/564.5 |
| 3,842,448 A | * | 10/1974 | Kahn | A61C 17/14 4/263 |

(Continued)

*Primary Examiner* — Timothy A Stanis
*Assistant Examiner* — Matthew R Moon
(74) *Attorney, Agent, or Firm* — Loza & Loza LLP; Kevin L. Soules

(57) ABSTRACT

The present invention is an oral hygiene system for providing pressurized water to a person's teeth or gums for oral hygiene. The oral hygiene system includes a main valve assembly, a filter assembly, a pressure tank assembly, a syphon assembly and a waterpik assembly. The main valve assembly is connectable to a water line, and includes a valve unit for controlling water flow. The filter assembly includes a filter cartridge, and is in fluid communication with the main valve assembly. The pressure tank assembly is in fluid communication with the filter assembly. The syphon assembly is capable of storing a liquid, and can include a syphon tube capable of dispensing the liquid into the water received from the pressure tank assembly. The waterpik assembly is in fluid communication with the syphon assembly, and is capable of allowing a user to provide pressurized water to a person's teeth or gums.

16 Claims, 4 Drawing Sheets

(56) References Cited

U.S. PATENT DOCUMENTS

| | | | | |
|---|---|---|---|---|
| 3,852,918 | A * | 12/1974 | Black | B24C 7/0053 451/99 |
| 3,964,112 | A * | 6/1976 | Plowman | A61C 17/14 433/97 |
| 4,193,520 | A * | 3/1980 | Duffield | E03C 1/046 222/133 |
| 4,601,709 | A * | 7/1986 | Kabbaby | E03C 1/046 604/150 |
| 4,725,232 | A * | 2/1988 | Hatakeyama | A61C 1/0038 433/126 |
| 4,883,086 | A * | 11/1989 | Lejnar | B01F 5/0496 137/399 |
| 5,312,251 | A * | 5/1994 | Jackson | A61C 3/025 433/88 |
| 5,393,228 | A * | 2/1995 | Policicchio | A61C 3/025 433/88 |
| 5,626,291 | A * | 5/1997 | Flinn | B01F 5/0413 239/310 |
| 5,626,472 | A * | 5/1997 | Pennetta | A61C 17/0214 433/80 |
| 5,685,028 | A * | 11/1997 | Miller | E03C 1/20 4/443 |
| 5,935,431 | A * | 8/1999 | Korin | A61L 2/10 210/205 |
| 6,264,119 | B1 * | 7/2001 | Truong | A61C 1/0076 15/29 |
| 7,980,923 | B2 * | 7/2011 | Olmo | A61C 3/025 433/215 |
| 8,210,846 | B2 * | 7/2012 | Duineveld | A61C 17/0202 433/85 |
| 2003/0013063 | A1 * | 1/2003 | Goldman | A61C 1/0084 433/80 |
| 2005/0101893 | A1 * | 5/2005 | Hippensteel | A61C 17/0214 601/162 |
| 2007/0148615 | A1 * | 6/2007 | Pond | A61C 1/0084 433/80 |
| 2007/0160951 | A1 * | 7/2007 | Bolognini | A61C 1/0076 433/80 |
| 2008/0096161 | A1 * | 4/2008 | Cain | A61C 17/0217 433/80 |
| 2012/0045730 | A1 * | 2/2012 | Sayder | A61C 1/0046 433/29 |

* cited by examiner

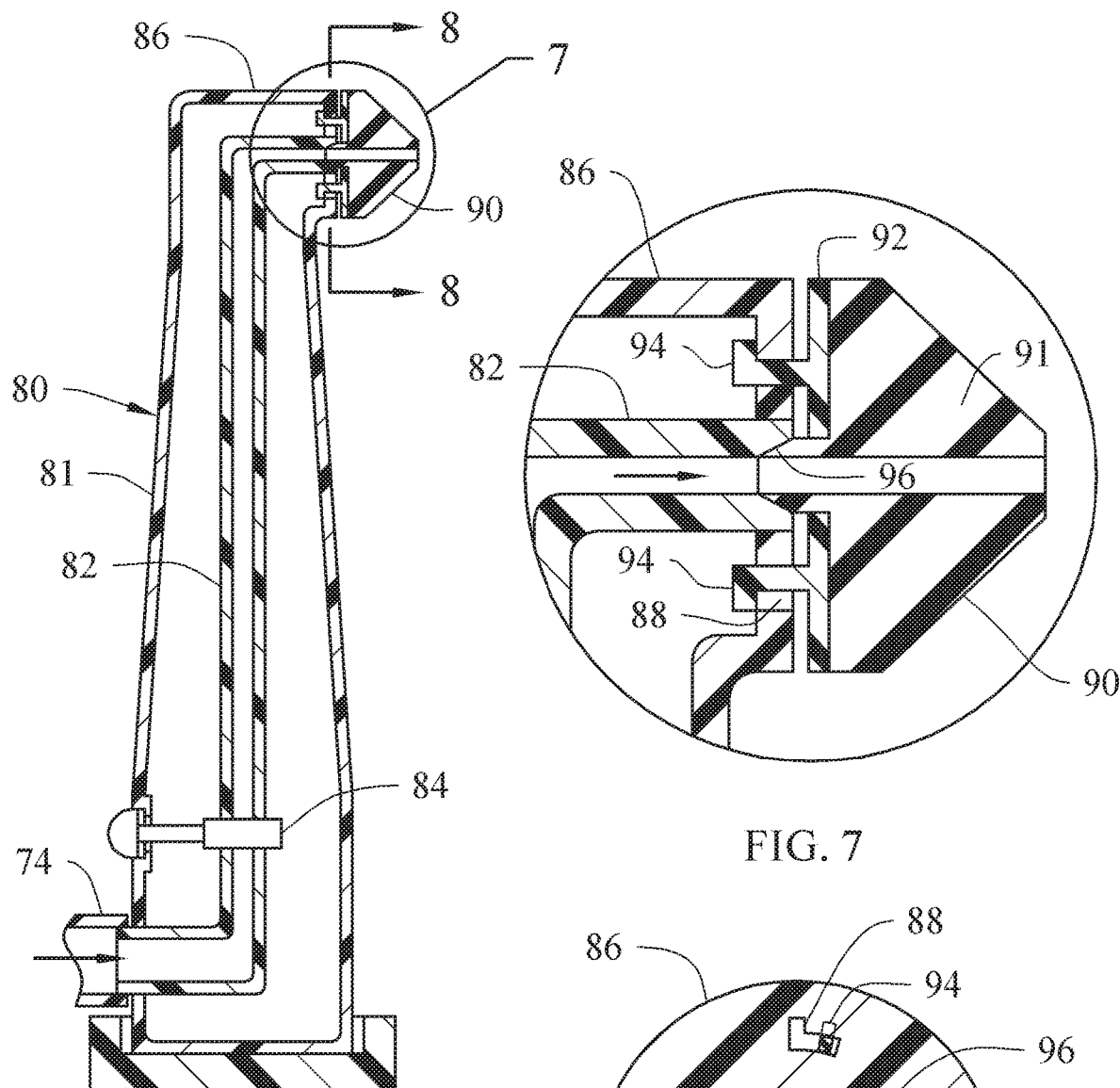
FIG. 6
FIG. 7
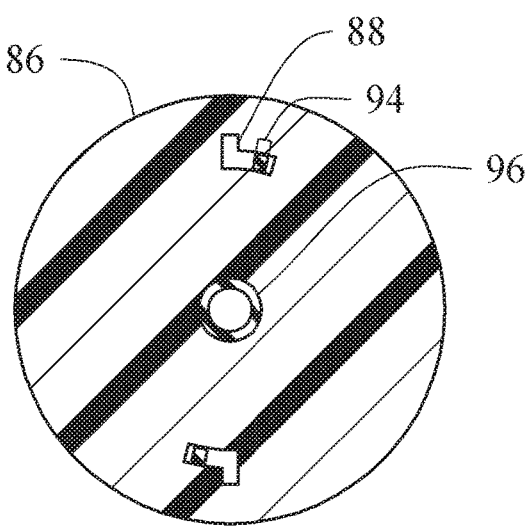
FIG. 8

US 10,524,888 B1

ORAL HYGIENE SYSTEM

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

FIELD OF THE INVENTION

The present invention relates to an oral hygiene system for use in connection with providing pressurized water to a person's teeth or gums for oral hygiene purposes by retrofitting the system to an existing sink water line.

DESCRIPTION OF THE PRIOR ART

A leading factor of tooth decay, gum disease and foul breath is food debris left in the mouth. So cleaning residual food from the mouth is an important measure for the prevention of oral diseases and proper oral hygiene. Many oral hygiene aids are known, such as toothbrushes, dental floss, oral irrigators, waterpik etc.

The use of oral irrigators is known in the prior art. Various water irrigating oral hygiene devices have been in the market, with some being attachable to an adjacent faucet or self-contained units. Oral irrigators typically are used to clean a user's teeth or gums by discharging a pressurized fluid stream into a user's oral cavity. Many oral irrigators include electrical components, such as batteries, a motor, or the like. Often oral irrigators are used in a wet environment, such as a bathroom and some users may even take the irrigators into the shower or bath, but conventional oral irrigators are not waterproof, merely water resistant. Hence, conventional oral irrigators may be protected from splashes and incidental fluid contact, but as they are not waterproof may not protect electronic components when submersed in water or exposed to large amounts of water. When water and other fluids reach the electronic components, the fluids can cause these electronic components to malfunction. These known oral irrigators are also costly to manufacture and maintain, which may include housings that are heavy to hold and manipulate.

While the above-described devices fulfill their respective, particular objectives and requirements, the aforementioned patents do not describe an oral hygiene system that provides pressurized water to a person's teeth or gums for oral hygiene purposes by retrofitting the system to an existing sink water line.

Therefore, a need exists for a new and improved oral hygiene system that can be used for providing pressurized water to a person's teeth or gums for oral hygiene purposes by retrofitting the system to an existing sink water line. In this regard, the present invention substantially fulfills this need. In this respect, the oral hygiene system according to the present invention substantially departs from the conventional concepts and designs of the prior art, and in doing so provide an apparatus primarily developed for the purpose of providing pressurized water to a person's teeth or gums for oral hygiene purposes by retrofitting to an existing sink water line.

BRIEF SUMMARY OF THE INVENTION

In view of the foregoing disadvantages inherent in the known types of oral irrigators now present in the prior art, the present invention provides an improved oral hygiene system, and overcomes the above-mentioned disadvantages and drawbacks of the prior art. As such, the general purpose of the present invention, which will be described subsequently in greater detail, is to provide a new and improved oral hygiene system and method which has all the advantages of the prior art mentioned heretofore and many novel features that result in an oral hygiene system which is not anticipated, rendered obvious, suggested, or even implied by the prior art, either alone or in any combination thereof.

To attain this, the present invention essentially comprises an oral hygiene system for providing pressurized water to a person's teeth or gums. The oral hygiene system includes a main valve assembly, a filter assembly, a pressure tank assembly, a syphon assembly and a waterpik assembly.

The main valve assembly can be connectable to and in fluid communication with at least one water line. The main valve assembly can include a valve unit having a configuration capable of controlling a flow of water from the water line.

The filter assembly can include a filter cartridge. The filter assembly is in fluid communication with an output of the main valve assembly.

The pressure tank assembly is in fluid communication with an output of the filter assembly.

The syphon assembly is capable of storing a liquid, and can include a syphon tube having a configuration capable of dispensing the liquid into the water received from an output of the pressure tank assembly.

The waterpik assembly is in fluid communication with the syphon assembly. The waterpik assembly can have a configuration capable of allowing a user to provide pressurized water to a person's teeth or gums.

The oral hygiene system can include a check valve associated with the output of the filter assembly or an input of the pressure tank assembly. The check valve having a configuration capable of maintaining a predetermined pressure in the pressure tank assembly.

The oral hygiene system can further include a pressure control valve associated with the output of the pressure tank assembly.

There has thus been outlined, rather broadly, the more important features of the invention in order that the detailed description thereof that follows may be better understood and in order that the present contribution to the art may be better appreciated.

The invention may also include a syphon valve having a configuration capable of extending into the syphon tube and controlling the liquid exiting the syphon tube that is stored in the syphon assembly. There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved oral hygiene system that has all of the advantages of the prior art oral irrigators and none of the disadvantages.

It is another object of the present invention to provide a new and improved oral hygiene system that may be easily and efficiently manufactured and marketed.

An even further object of the present invention is to provide a new and improved oral hygiene system that has a low cost of manufacture with regard to both materials and labor, and which accordingly is then susceptible of low prices of sale to the consuming public, thereby making such oral hygiene system economically available to the buying public.

Still another object of the present invention is to provide a new oral hygiene system that provides in the apparatuses and methods of the prior art some of the advantages thereof, while simultaneously overcoming some of the disadvantages normally associated therewith.

Even still another object of the present invention is to provide an oral hygiene system for providing pressurized water to a person's teeth or gums for oral hygiene purposes. This allows for easy of oral hygiene using a system that can be retrofitted to existing sink water lines.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 6 is a cross-sectional view of the oral hygiene assembly of the present invention.

FIG. 7 is an enlarged cross-sectional view of the attachable tip of the oral hygiene assembly of the present invention.

FIG. 8 is a cross-sectional view of the oral hygiene assembly of the present invention taken along line 8-8 in FIG. 6.

The same reference numerals refer to the same parts throughout the various figures.

DETAILED DESCRIPTION OF THE INVENTION

Figure 1:
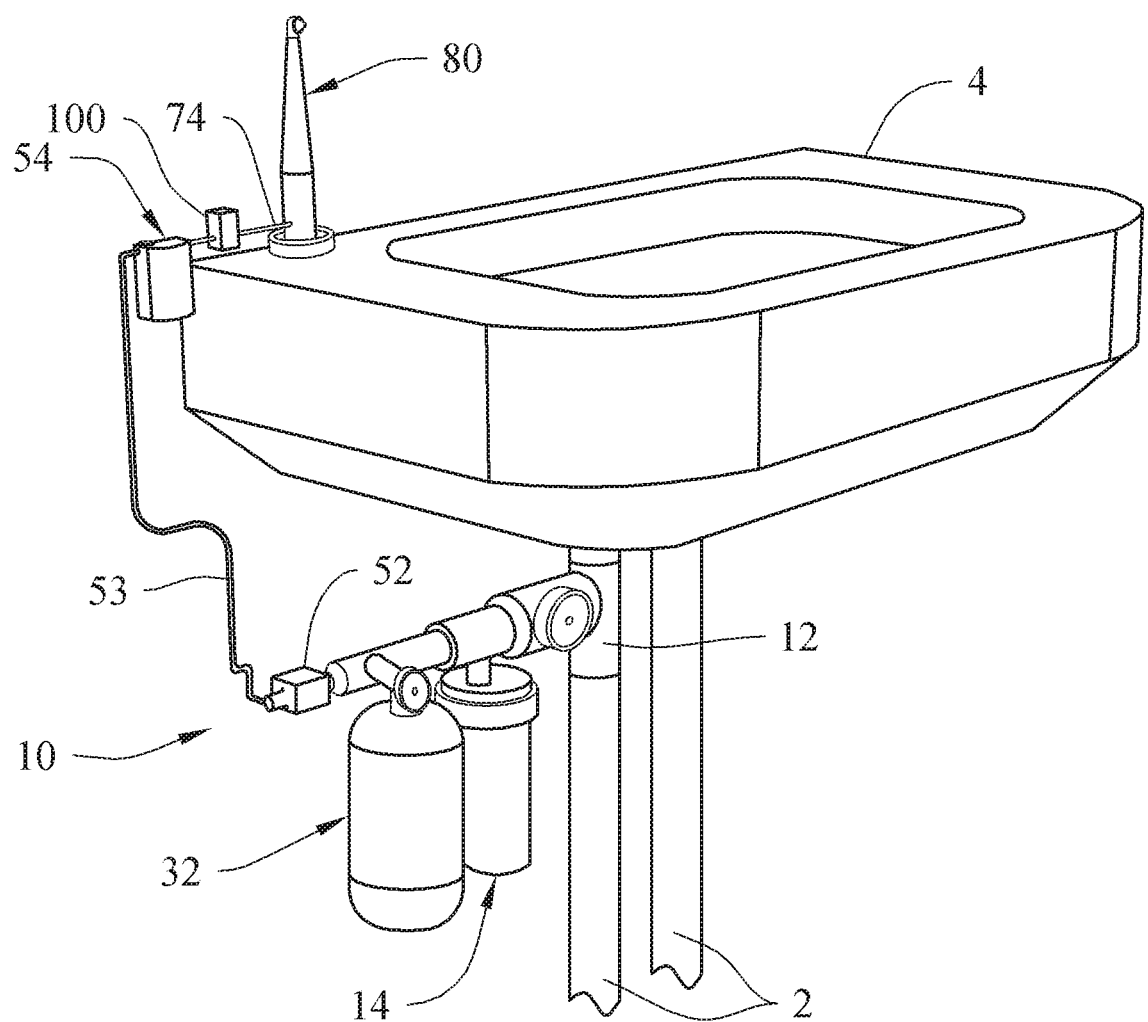
FIG. 1 is a perspective view of an embodiment of the oral hygiene system constructed in accordance with the principles of the present invention, with phantom lines depicting environmental structure.

Referring now to the drawings, and particularly to FIGS. 1-8, an embodiment of the oral hygiene system of the present invention is shown and generally designated by the reference numeral 10.

With reference to FIG. 1, a new and improved oral hygiene system 10 of the present invention for providing pressurized water to a person's teeth or gums for oral hygiene purposes is illustrated and will be described. More particularly, the oral hygiene system 10 broadly includes a main valve assembly 12, a filter assembly 14, a pressure tank assembly 32, a syphon assembly 54, and a waterpik assembly 80. The oral hygiene system 10 can be retrofittable to an existing sink 4 by connected the main valve assembly 12 to either the hot or cold water line 2. It can be appreciated that the oral hygiene system 10 can be combined into a sink and water line module for providing an all in one unit. The oral hygiene system 10 is operated by water pressure supplied by the water line 2, and thus can be used during power outages. The powering of the oral hygiene system 10 by remote water pressure further prolongs the life span of the oral hygiene system 10 since no complex or numerous electrical components are needed. Suitable mounting brackets can be utilized to support components of the oral hygiene system 10 to any part of the sink 4 or to a planar surface, such as but not limited to, a wall, a door, a cabinet and the like.

The main valve assembly 12 includes a branch coupler adapted to connect to the water line 2 while diverting a portion of water flow to the oral hygiene system 10. The branch coupler can be connected to the water line 2 by way of any known plumbing connection means, such as but not limited to, threads, adhesive, press fittings, inter-engaging means and the like. The main valve assembly 12 further includes a main valve unit for controlling the water flow from the water line 2 to the oral hygiene system 10. The main valve unit can be any valve capable of controlling water flow from the water line 2. It can be appreciated that the main valve assembly 12 can be operated manually or by an electrical drive means.

Figure 2:
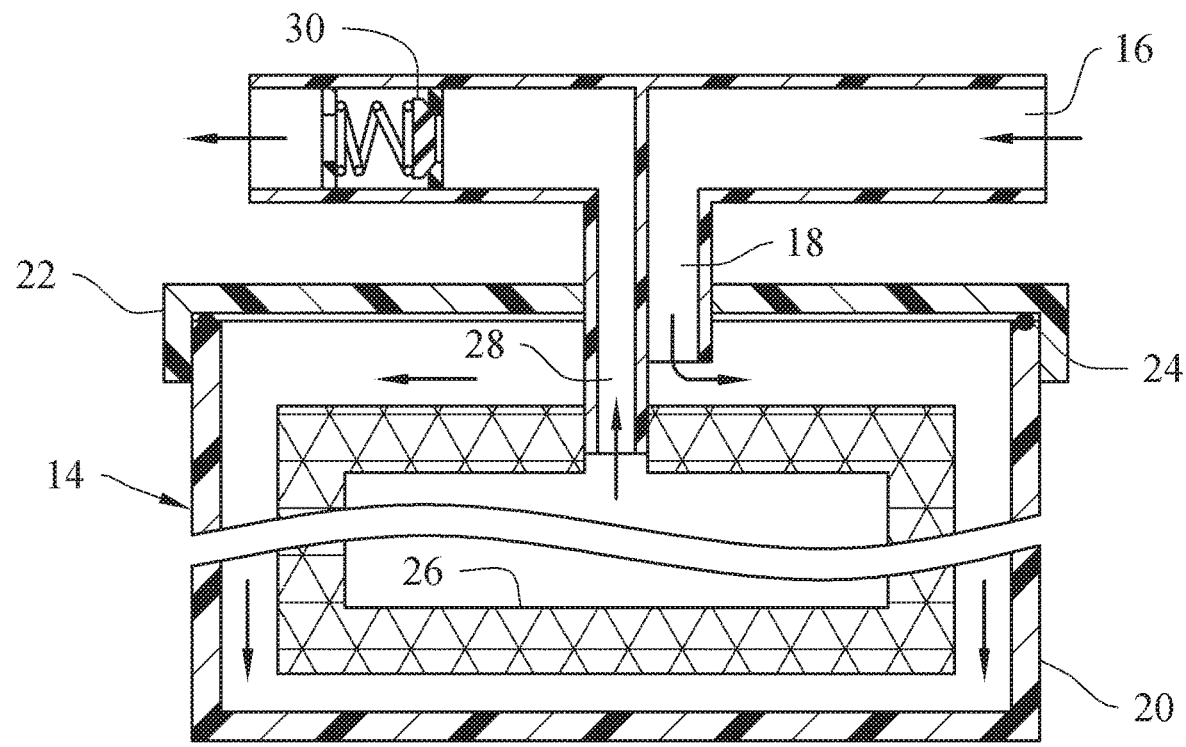
FIG. 2 is a cross-sectional view of the filter assembly of the present invention.

With reference to FIG. 2, the filter assembly 14 can include a filter input plumbing 16, a filter container 20 featuring a removable filter lid 22, a filter cartridge 26 receivable in the filter container 20, and a filter output plumbing 28. The filter input plumbing 16 can include at least one first end connectable to and in fluid communication with an output of the main valve assembly 12, and at least one second end received through the filter lid 22 and in fluid communication with an interior of the filter container 20. The second end of the filter input plumbing 16 that is received through the filter lid 22 is configured to exit the water flow exterior of the filter cartridge 26. This configuration allows the water flow to enter the filter container 20 and travel around and then through the filter cartridge 26, thereby filtering the water.

The filter output plumbing 28 can include at least one first end received through the filter lid 22 and in fluid communication with an interior of the filter cartridge 26, and a second end for outputting the water flow from the filter container 20. The first end of the filter output plumbing 28 can be sealably coupled to an opening in the filter cartridge 26, thereby allowing the filtered water to exit the filter cartridge 26.

A check valve 30 can be associated with the filter output plumbing to maintain pressure downstream of the filter assembly 14. It can be appreciated that the check valve 30 can be associated with the main valve assembly 12, the filter input plumbing 16 or any location upstream of the pressure tank 34. The check valve 30 can include a wall featuring an orifice, and a biased plunger removably and sealingly associated with the orifice, thereby creating a one way flow valve. It can be appreciated that other check or one-way valve means can be used without deviated from the scope of the present invention.

Figure 3:
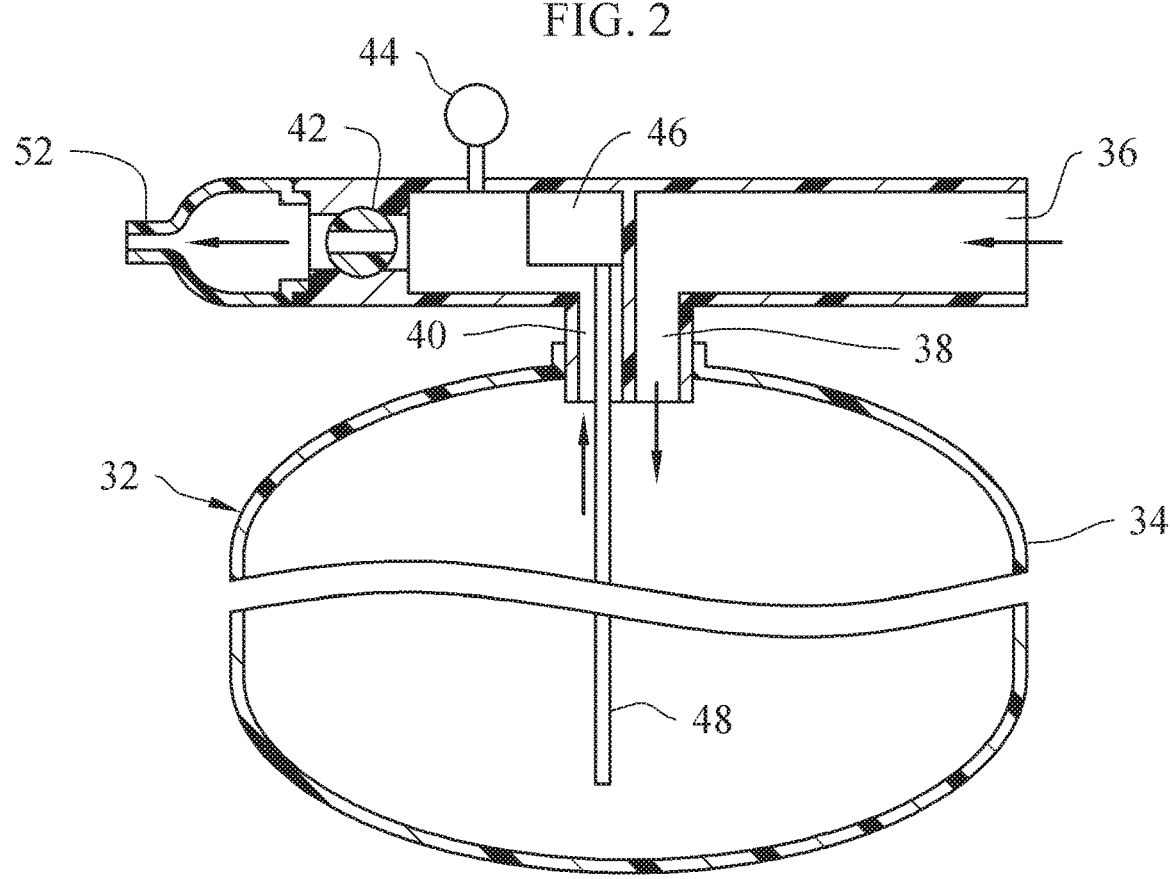
FIG. 3 is a cross-sectional view of the pressure tank assembly of the present invention.

With reference to FIG. 3, the pressure tank assembly 32 can include a pressure tank 34, a pressure tank input plumbing 36, and a pressure tank output plumbing 40. The pressure tank 34 can be any closed container capable of retaining water and at an elevated pressure, and can include multiple tanks connected together in series or parallel.

The pressure tank input plumbing 36 can include at least one first end connectable to and in fluid communication with the second end of the filter output plumbing 28, and a second end in fluid communication with an interior of the pressure tank 34. The pressure tank output plumbing 40 can include a first end in fluid communication with the interior of the pressure tank 34, and a second end for outputting the water flow from the pressure tank 34.

A pressure control valve 42 can be associated with any portion of the pressure tank output plumbing 40. The pressure control valve 42 can be any valve means capable of controlling the water flow and pressure exiting the pressure tank 34 without deviated from the scope of the present invention. It can be appreciated that the pressure control valve 42 can be integral with the pressure tank output plumbing 40 or can be a separate valve unit connected to the second end of the pressure tank output plumbing 40.

A pressure gauge 44 can be connected to any part of the pressure tank assembly 32 to read and display the pressure from the interior of the pressure tank 34.

A connection hub 52 can be connected to and in fluid communication with the second end of the pressure tank output plumbing 40 or the pressure control valve 42. The connection hub 52 has a configuration capable of allowing a flexible hose 53 to be easily and removably connected thereto.

A pump 46 can be located in the pressure tank output plumbing 40, and can have a configuration capable of pumping water from the interior of the pressure tank 34 to the pressure tank output plumbing 40. It can be appreciated that the pump 46 can alternatively be a pressurizing pump that increases the pressure in the pressure tank 34 to produce a motive force on the water to flow through the pressure tank output plumbing 40.

It can be appreciated, without deviated from the scope of the present invention, that the main valve assembly 12, the filter assembly 14 and/or the pressure tank assembly 32 can be mounted or located under the sink 4. With a flexible hose 53 allowing for adjustable placement of the syphon assembly 54 and/or the waterpik assembly 80.

Figure 4:
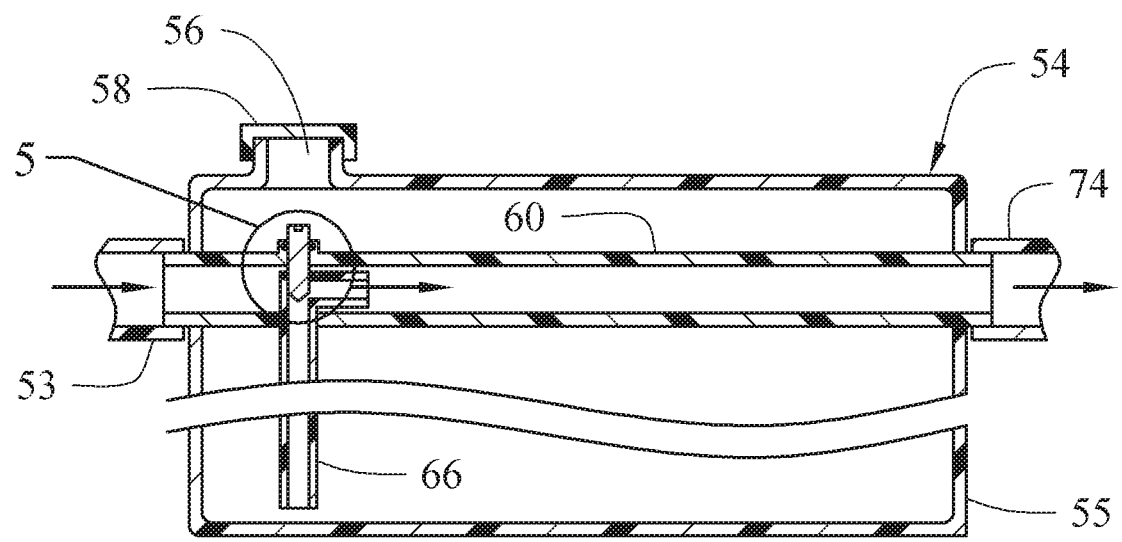
FIG. 4 is a cross-sectional view of the syphon assembly of the present invention.
Figure 5:
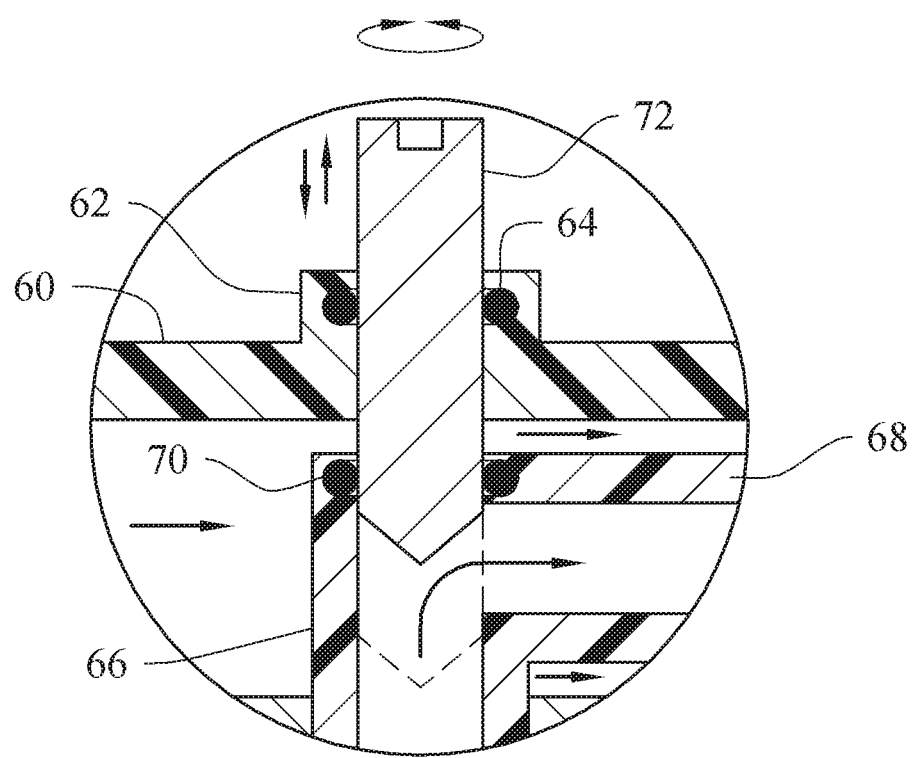
FIG. 5 is an enlarged cross-sectional view of the adjustable syphon valve of the syphon assembly of the present invention.

With reference to FIGS. 4 and 5, the syphon assembly 54 can include a syphon container 55, a conduit 60, and a syphon tube 66. The syphon container 55 is capable of storing a liquid, such as but not limited to, mouthwash, medicament etc. The syphon container 55 can further include a container neck 56 featuring a container neck opening therethrough, and a cap 58 associated with the container neck 56 to cover and seal the container neck opening.

The conduit 60 can pass through the syphon container 55 so that a first end is in fluid communication with the flexible hose 53, and a second end exits the syphon container 55 at an opposite end thereof. The conduit 60 is configured to receive the water flow from the pressure tank assembly 32 and allow the water to flow therethrough to its second end for exiting. The conduit 60 further includes a conduit neck 62 defining a conduit neck opening therethrough, and a conduit neck seal 64. The conduit neck 62 extends from the conduit 60 in a direction toward and aligned with the container neck opening of the container neck 56. Consequently, the container neck opening of the container neck 56 and the conduit neck opening of the conduit neck 62 are aligned.

The syphon tube 66 extends into the interior of the syphon container 55 with a portion of the syphon tube 66 extending into the conduit 60. The syphon tube 66 can include a dispensing extension 68 located within and parallel with the conduit 60, and extending in direction of the water flow or towards the second end of the conduit 60. The syphon tube 66 or the dispensing extension 68 defines a syphon tube opening that is aligned with the conduit neck opening of the conduit neck 62. A syphon opening seal 70 is associated with the syphon tube opening. It can be appreciated that the container neck opening of the container neck 56, the conduit neck opening of the conduit neck 62 and the syphon tube opening are all aligned with each other.

A syphon valve 72 can be received through the conduit neck opening of the conduit neck 62 and the syphon tube opening. When installed, the syphon valve 72 is consequently aligned with the container neck opening of the container neck 56, allowing for easy access and engagement of the syphon valve 72 from outside the syphon container 55. The syphon valve 72 includes a threaded section that engages with a threaded section of the conduit neck 62, allowing the syphon valve 72 to be adjustable advanced or retracted through the syphon tube opening and the syphon tube 66. The syphon valve 72 has a configuration capable of extending into the syphon tube 66 and controlling the liquid flowing from the interior of the syphon container 55 and into the dispensing extension 68.

As best illustrated in FIG. 5, in an open or partially opened position a tapered end of the syphon valve 72 is removed from the syphon tube 66, allowing liquid to flow there past and into the dispensing extension 68. In a closed position, as illustrated by the dashed lines, the tapered end is fully received in the syphon tube 66, closing off the dispensing extension 68 and preventing liquid from entering the dispensing extension 68. The conduit neck seal 64 and the syphon opening seal 70 prevent liquid from entering the conduit 60 except from through the dispensing extension 68.

A space is defined between an exterior side of the dispensing extension 68 and an interior side of the conduit 60, allowing the water from the pressure tank assembly 32 to flow past and around the dispensing extension 68 and through the conduit 60. Consequently, this produces negative pressure at a free end of the dispensing extension 68 that syphons the liquid through the syphon tube 66 and out the dispensing extension 68 to combine with the water flowing toward the second end of the conduit 60.

A flexible waterpik hose 74 can be connected to and in fluid communication with the second end of the conduit 60. A hose retracting mechanism 100 can be used to retract the waterpik hose 74 when not in use.

With reference to FIGS. 6-8, the waterpik assembly 80 can include a body 81, a waterpik conduit 82, and a tip 90. The waterpik assembly 80 can be supported by a base 78, which can be mounted to a wall, door or a surface of the sink 4.

The body 81 can include a head extension 86, and an ergonomic configuration allowing for easy grasping and manipulation by a user. The head extension 86 extends away from a longitudinal axis of the body 81, and can include a surface featuring a plurality of slots 88 defined through the surface of the head extension 86.

The waterpik conduit 82 has a first end that can be connected to and in fluid communication with the second end of the conduit 60 by way of the waterpik hose 74, and a second end in fluid communication with the surface of the head extension 86.

A waterpik valve 84 can be associated with the waterpik conduit 82 and capable of controlling water flowing through the waterpik conduit 82. The waterpik valve 84 can be activated by a button or switch.

The tip 90 can be removably connected to the surface of the head extension 86. The tip 90 can include a tip body 91, and a back plate 92. The back plate 92 includes a plurality of locking keys 94 extending therefrom. The locking keys 94 each are receivable in corresponding slots 88, respectively, and have a configuration capable of retaining the tip 90 toward the surface of the head extension 86 when the tip 90 is rotated in a predetermined direction. Further rotation of the tip 90 will advance the tip 90 toward the surface of the head extension 86 by way of threads or angled surfaces associated with the slots 88.

The tip body 91 can be made of a flexible material, such as but not limited to rubber, silicon or the like. The tip body 91 further includes a connection portion 96 extending through the back plate 92, and features a tapered end portion. A passage is defined through the tip body 91 and the connection portion 96.

The tapered end of the connection portion 96 has a configuration capable of sealably contacting with a corresponding tapered portion of the second end of the waterpik conduit 82 when the tip 90 is installed against the head extension 86. This positions the passage of the tip 90 to be in fluid communication with the waterpik conduit 82, allowing the water to flow out of the tip 90.

It can be appreciated that a plurality of tips can be provided with the oral hygiene system 10 as a kit or separately, and with each tip being similar or with different configurations and/or materials. It can be further appreciated that the passage defined through the tip 90 can include vanes, baffles or rotors configured to impart a vibrational or rotational action to the tip body 91.

Still further, it can be appreciated that the main valve assembly 12, the filter assembly 14 and the pressure tank assembly 32 can be arranged as an integral unit or separate units each connectable to the other.

In use, it can now be understood that the main valve assembly 12 will be installed to the hot or cold water line 2, and the main valve unit is operated to allow water to flow into the filter assembly 14. Upon operation of the main valve unit, water will flow through the filter input plumbing 16, into the filter container 20 and exterior of the filter cartridge 26. The water will then flow through the filter cartridge 26, through the filter output plumbing 28 and then through the check valve 30.

After the check valve 30 the water will flow through the pressure tank input plumbing 36 and into the pressure tank 34. Pressure will build inside the pressure tank 34 in consequence of the check valve 30. The pressure and water flow exiting the pressure tank 34 is controlled by operation of the pressure control valve 42.

Upon activation of the waterpik valve 84, the water will then flow out from the pressure tank output plumbing 36 and through the conduit 60. If the user wishes to add an additive liquid like mouthwash, then the user would operate the syphon valve 72 allowing liquid in the syphon container 55 to be pulled up the syphon tube 66 and dispensed into the conduit 60.

The water will then flow through the waterpik conduit 82, through the tip passage and out the tip 90 for use with oral hygiene or other cleaning purposes.

While embodiments of the oral hygiene system have been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable sturdy material may be used instead of the above-described. And although providing pressurized water to a person's teeth or gums for oral hygiene purposes have been described, it should be appreciated that the oral hygiene system herein described is also suitable for providing pressurized water for any cleaning purposes.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An oral hygiene system for providing pressurized water to a person's teeth or gums, said oral hygiene system comprising:
    a main valve assembly connectable to and in fluid communication with at least one water line, said main valve assembly including a valve unit having a configuration capable of controlling a flow of water from the water line;
    a filter assembly including a filter cartridge, said filter assembly being in fluid communication with a main valve assembly output;

a pressure tank assembly being in fluid communication with a filter assembly output;

a syphon assembly capable of storing a liquid, said syphon assembly including a syphon tube having a configuration capable of dispensing the liquid into water received from a pressure tank assembly output, wherein the syphon assembly further comprises a conduit passing through a syphon container, the conduit being in fluid communication with the pressure tank assembly, the conduit further comprising a neck extending from the conduit, a neck opening defined through the neck and aligned with a syphon container opening, and a neck seal associated with the neck opening;

wherein a portion of said syphon tube extends into said conduit, said portion of said syphon tube including a dispensing extension located within and parallel with said conduit;

wherein said syphon tube further includes a syphon tube opening and a syphon tube seal, said syphon tube opening being aligned with said neck opening and a syphon container opening, said syphon tube seal being associated with said syphon tube opening;

wherein a syphon valve is receivable through said neck opening and said syphon tube opening, said syphon valve having a configuration capable of extending into said syphon tube and controlling the liquid flowing into said dispensing extension; and a water flosser assembly in fluid communication with said syphon assembly.

2. The oral hygiene system of claim 1 further comprising a check valve configured between said filter assembly output and a pressure tank assembly input.

3. The oral hygiene system of claim 2 further comprising a pressure control valve associated with said pressure tank assembly output.

4. The oral hygiene system of claim 1, wherein said filter assembly further comprising:
a filter container having a configuration capable of receiving said filter cartridge;
a filter input plumbing in fluid communication with said main valve assembly output and an interior of said filter container exterior of said filter cartridge; and
a filter output plumbing in fluid communication with an interior of said filter cartridge.

5. The oral hygiene system of claim 4, wherein said filter assembly further comprises a filter lid connectable to said filter container, wherein a portion of said filter input plumbing and a portion of said filter output plumbing are received through said filter lid.

6. The oral hygiene system of claim 1, wherein said pressure tank assembly further comprising:
a pressure tank;
a pressure tank input plumbing in fluid communication with said filter assembly and an interior of said pressure tank; and
a pressure tank output plumbing in fluid communication with said interior of said pressure tank.

7. The oral hygiene system of claim 6, wherein said pressure tank assembly further comprises a pressure gauge.

8. The oral hygiene system of claim 6 further comprising a connection hub in fluid communication with said pressure tank output plumbing, and a hose in fluid communication with said connection hub and said syphon assembly.

9. The oral hygiene system of claim 1, wherein said syphon assembly further comprises:

said syphon container having a configuration capable of storing the liquid, said syphon container including a syphon container opening defined through said syphon container.

10. The oral hygiene system of claim 9, wherein a space is defined between said dispensing extension and an interior surface of said conduit capable of allowing water flowing from said pressure tank assembly to flow past said dispensing extension, said conduit and said dispensing extension have a configuration capable of producing negative pressure at a free end of said dispensing extension to syphon the liquid through said syphon tube and out said dispensing extension to combine with water flowing through said conduit.

11. The oral hygiene system of claim 1, wherein a portion of said syphon valve is aligned with said syphon container opening.

12. The oral hygiene system of claim 1, wherein the water line is associated with a sink.

13. An oral hygiene system for providing pressurized water to a person's teeth or gums, said oral hygiene system comprising:
a main valve assembly connectable to and in fluid communication with at least one water line, said main valve assembly including a valve unit having a configuration capable of controlling a flow of water from the water line;
a filter assembly including a filter cartridge, said filter assembly being in fluid communication with a main valve assembly output;
a pressure tank assembly being in fluid communication with a filter assembly output;
a syphon assembly capable of storing a liquid, said syphon assembly including a syphon tube having a configuration capable of dispensing the liquid into water received from a pressure tank assembly output; and
a water flosser assembly in fluid communication with said syphon assembly said water flosser assembly further comprising:
a conduit in fluid communication with said syphon assembly by way of a hose; a body including a head extension;
a tip in fluid communication with said conduit, said tip further comprising a back plate including a plurality of locking keys extending from said back plate, wherein said tip has a configuration capable of dispensing the water; and said tip further comprising a tip body, a connection portion, and a passage defined through said tip body and said connection portion, wherein, at least a portion of said connection portion extends through said back plate, wherein said locking keys each are receivable in slots defined in a surface of said head extension, respectively, said locking keys and said slots each have a configuration capable of retaining said tip against said surface of said head extension when said tip is rotated in a predetermined direction.

14. The oral hygiene system of claim 13, wherein said water flosser assembly further comprises:
a valve associated with said conduit, said valve having a configuration capable of controlling water flowing through said conduit.

15. The oral hygiene system of claim 13, wherein said tip is removably connected to said head extension.

16. The oral hygiene system of claim 15 wherein said connection portion has a configuration capable of sealably contacting with said conduit when said tip is installed against said surface so that said passage is in fluid communication with said conduit.

* * * * *